United States Patent [19]

Ibarra

[11] 4,202,057
[45] May 13, 1980

[54] DEVICE FOR RECEIVING AND DISPOSING OF URINE FROM BEDRIDDEN WOMEN

[76] Inventor: Guillermo N. Ibarra, Calle General San Martin No. 222, Col. Reforma, Guadalajara, Jal., Mexico

[21] Appl. No.: 939,776

[22] Filed: Sep. 5, 1978

[51] Int. Cl.² ............................................. A61G 9/00
[52] U.S. Cl. ................................. 4/144.3; 128/761; 128/295
[58] Field of Search ................... 4/144.1, 144.3, 144.2, 4/144.4; 128/295, 294, 2 F

[56] References Cited

U.S. PATENT DOCUMENTS

| | | | |
|---|---|---|---|
| 2,490,969 | 12/1949 | Kinyon | 4/144.3 |
| 3,000,015 | 9/1961 | Hart | 4/144.3 |
| 3,995,329 | 12/1976 | Williams | 4/144.4 |
| 4,023,216 | 5/1977 | Li | 4/144.3 |

*Primary Examiner*—Lenard A. Footland
*Attorney, Agent, or Firm*—Wigman & Cohen

[57] ABSTRACT

A device for receiving and disposing of urine from bedridden women is disclosed. The device comprises a receptacle which anatomically conforms to the shape of the female genitalia so as to prevent dripping and is provided with a urine receiving opening and a urine discharge tube.

5 Claims, 4 Drawing Figures

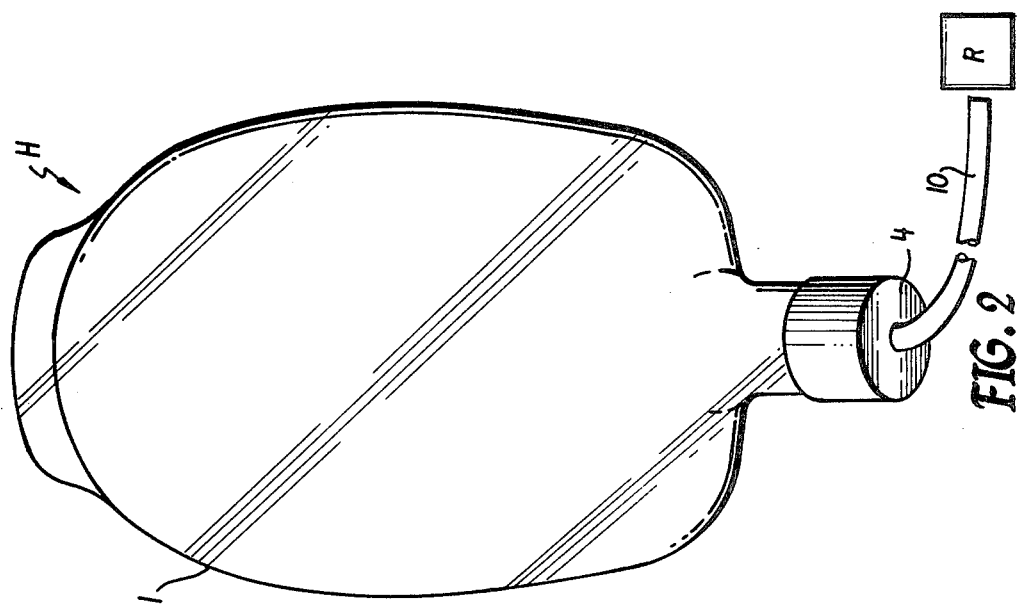
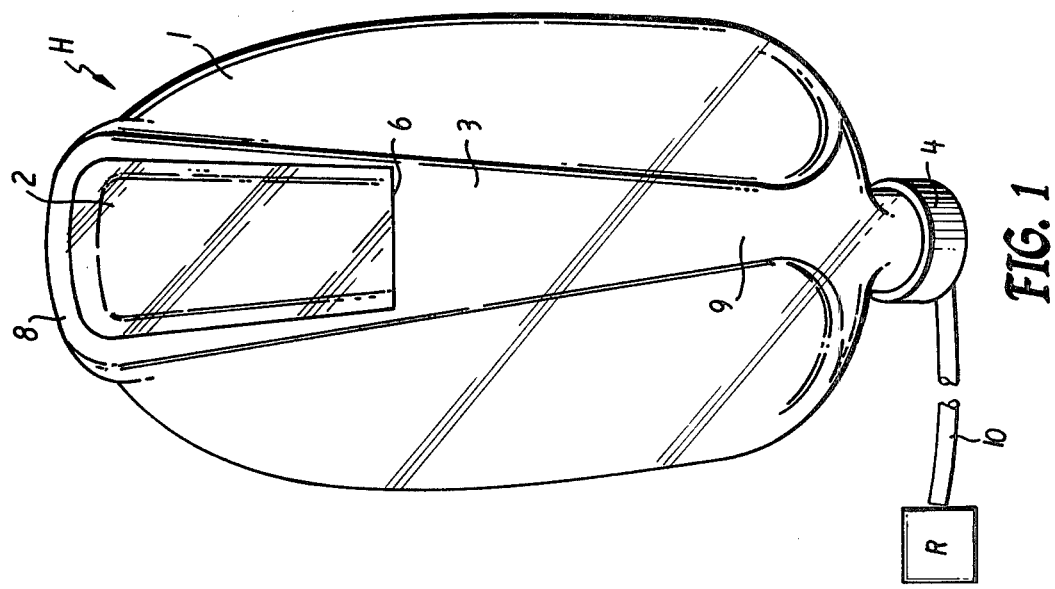

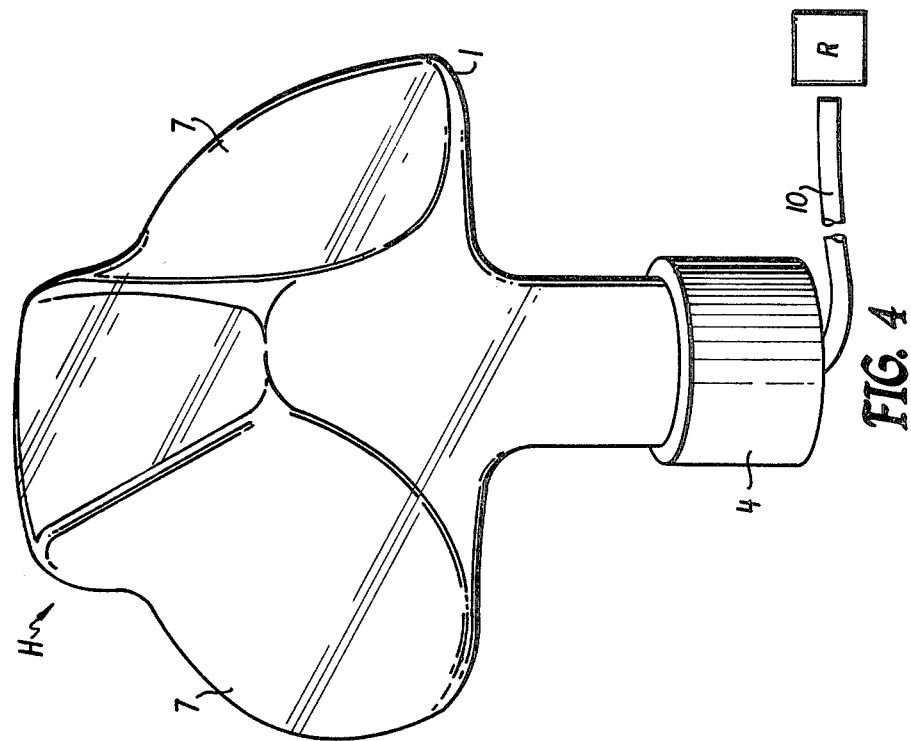
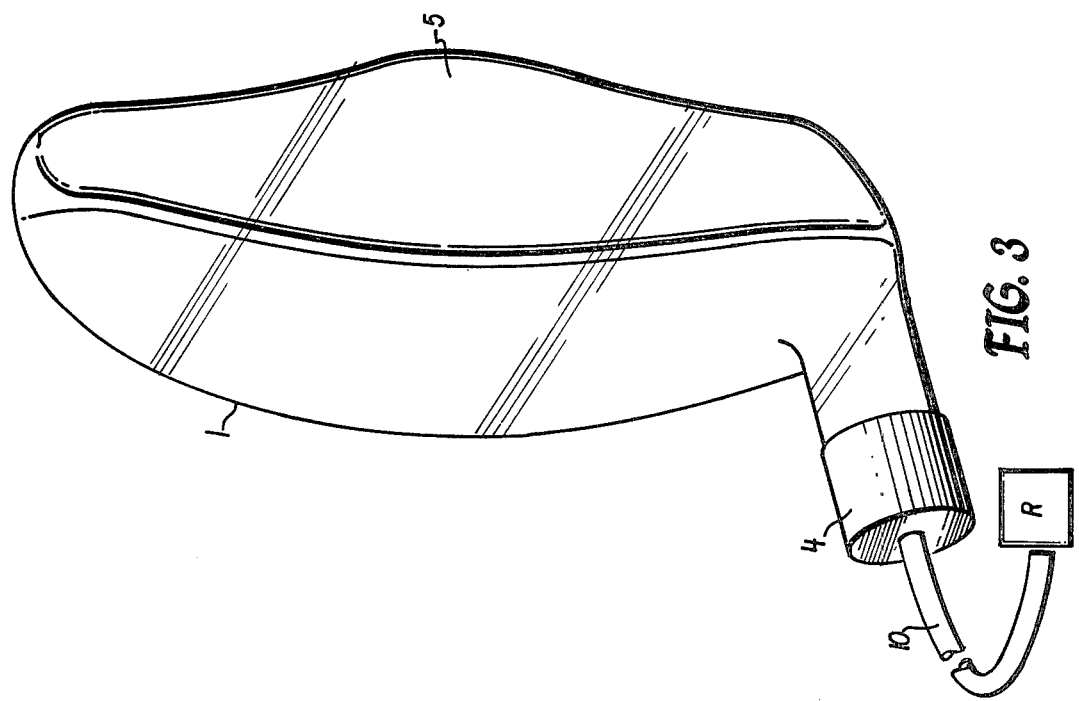

DEVICE FOR RECEIVING AND DISPOSING OF URINE FROM BEDRIDDEN WOMEN

BACKGROUND OF THE INVENTION

The present invention relates to a device for receiving and disposing of urine from women, who, through some illness, are bedridden.

In the case of an illness which requires the person to be confined to bed, the use of the device according to the present invention satisfactorily replaces the so-called "commode".

Normally, except in cases of extreme seriousness, the woman simply asks for the "commode" from the persons attending her, but generally she arranges the receptacle herself, and after using it she cannot dry her own parts, since the urine drips away as a result of the uncomfortable position, thus causing chafing and sores.

SUMMARY AND OBJECTS OF THE INVENTION

A primary objective of the present invention is to eliminate the inconveniences associated with the known "commode".

Another objective of the present invention is to provide a device which a bedridden woman can use directly, without the assistance of a second person.

Another objective of the present invention is to provide a device which, because of its anatomical form, prevents the dripping away of urine and its disagreeable consequences.

The device of the present invention is made of a smooth material with no rough edges, for example, a synthetic plastic, such as vinyl or any other material having similar characteristics, so as to avoid the possibility of producing lesions, and has a very special shape which is molded so as to anatomically conform to the female genitals.

BRIEF DESCRIPTION OF THE DRAWINGS

To facilitate understanding the invention and its characteristic details, a description is given below with reference to the accompanying drawings as an illustration thereof. The reference symbols serve to indicate the same parts both in the figures provided and in the description.

FIG. 1 is a top view of the device,
FIG. 2 is a bottom view of the device,
FIG. 3 is a side view of the device, and
FIG. 4 is an end view of the device.

DESCRIPTION OF A PREFERRED EMBODIMENT

In FIG. 1, the device H has the shape of an ellipse, along the main axis of which a raised portion is provided in the shape of an isosceles triangle having rounded vertices. The raised portion has an opening 2 and a cover portion 3 which extends over approximately half its length from its smaller vertex 9 to its base 8.

FIG. 2 shows the position of the device H as applied to the bedridden patient as seen from the patient's feet. This figure shows a discharge tube 4 for the urine, which tube 4 is located at the rear part of the smaller vertex 9 of the raised portion. A flexible rubber tube 10 may be connected thereto in order to drain out the urine to a remote receptacle or commode.

FIG. 3 shows the widest part 5 of the device H corresponding to the narrowest part 6 (FIG. 1) of the urine-receiving opening 2.

FIG. 4 shows the grooves 7 of the device H which run lengthwise and curve from the base 1 up to the opening 2 for perfect anatomical adaptation to the person using it.

Although a preferred embodiment is specifically illustrated and described herein, it will be appreciated that many modifications and variations of the present invention are possible in light of the above teaching and within the pervue of the appended claims without departing from the spirit and intended scope of the invention.

What is claimed is:

1. A device for receiving and disposing of urine from bedridden women, comprising a receptacle having the shape of an ellipse along the major axis of which there is arranged a raised portion having approximately the shape of an isosceles triangle with slightly rounded vertices, an opening in said raised portion adjacent the base of said triangle, grooves provided in said receptacle on opposite sides of said raised portion, said grooves running lengthwise and curving from the base side of the receptacle up to the opening in the raised portion for anatomical adaptation to a bedridden woman using the receptacle and a urine discharge tube arranged on the base side of the receptacle opposite the raised portion and wherein the raised portion has a cover portion which extends over approximately half its length from its smaller vertex to the base of the isosceles triangle; and wherein the widest part of the receptacle corresponds to the narrowest part of the opening in the raised portion.

2. A device according to claim 1, wherein the receptacle has a shape which anatomically conforms to the female genitalia so as to prevent urine from dripping therefrom.

3. A device according to claim 1, including a flexible rubber tube means, connected to said discharge tube, for draining the urine, said discharge tube being arranged at an angle with respect to the receptacle to facilitate drainage.

4. A device according to claim 1, wherein said receptacle is made of a synthetic plastic.

5. A device according to claim 1, wherein the urine discharge tube is located at a rear part of the smaller vertex of the raised portion.

* * * * *